United States Patent [19]

Mitscher et al.

[11] Patent Number: 4,826,985

[45] Date of Patent: May 2, 1989

[54] INTERMEDIATES FOR PREPARATION OF RACEMATE AND OPTICALLY ACTIVE OFLOXACIN AND RELATED DERIVATIVES

[75] Inventors: Lester A. Mitscher, Lawrence, Kans.; Daniel T. Chu, Vernon Hills, Ill.

[73] Assignee: Abbott Laboratories, Abbott Park, Ill.

[21] Appl. No.: 216,063

[22] Filed: Jul. 7, 1988

Related U.S. Application Data

[62] Division of Ser. No. 858,532, Apr. 25, 1986, Pat. No. 4,777,253.

[51] Int. Cl.[4] .............................. C07D 215/22
[52] U.S. Cl. ................... 546/156; 544/101; 544/105; 560/37
[58] Field of Search ........................ 546/156

[56] References Cited

U.S. PATENT DOCUMENTS 4,578,473 3/1986 Domagala et al. ................. 546/156
4,692,454 9/1987 Mich et al. ........................ 546/156
4,777,175 10/1988 Culbertson et al. ................ 546/156

OTHER PUBLICATIONS

Grohe, et al., "Chemical Abstracts", vol. 107, 1987, col. 107:23351g.

Egawa, et al., "Chemical Abstracts", vol. 107, 1987, col. 107:39724s.

Mitscher, et al., "Chemical Abstracts", vol. 107, 1987, col. 107:198206r.

Egawa, et al., "Chemical Abstracts", vol. 108, 1988, col. 108:167489b.

Primary Examiner—Glennon H. Hollrah
Assistant Examiner—James H. Turnipseed
Attorney, Agent, or Firm—Robert W. Stevenson; Steven R. Crowley; Martin L. Katz

[57] ABSTRACT

A process for producing racemic or optically active compounds of the formula:

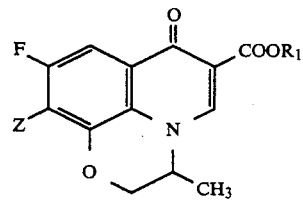

wherein $R_1$ is hydrogen, $C_1$ to $C_6$ alkyl or benzyl; and Z is amino or substituted amino. Also disclosed are intermediates useful in the process and methods for producing the intermediates.

4 Claims, No Drawings

INTERMEDIATES FOR PREPARATION OF RACEMATE AND OPTICALLY ACTIVE OFLOXACIN AND RELATED DERIVATIVES

This is a division of application Ser. No. 858,532, filed Apr. 25, 1986, now U.S. Pat. No. 4,777,253.

BACKGROUND OF THE INVENTION

This invention relates to novel methods of producing the racemate and enantiomers of 9-fluoro-3-methyl-10-substituted amino-7-oxo-2,3-dihydro-7H-pyrido[1,2,3-de]-1,4-benzoxazine-6-carboxylic acid compounds (A) and to compounds useful as intermediates in the production of the above benzoxazine-6-carboxylic acid compounds.

It is known that the racemate 9-fluoro-3-methyl-10-(4-methyl-1-piperazinyl)-7-oxo-2,3-dihydro-7H-pyrido[1,2,3-de], 1,4-benzoxazine-6-carboxylic acid (i.e. compounds of formula A wherein Z is N-methyl piperazinyl) exhibits antibacterial properties as described in European patent application serial No. 47,005 and in Japanese Application No. 82 46,986.

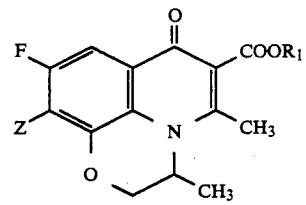

Ofloxacin, a compound of formula (A) wherein Z is N-methyl piperazinyl and $R_1=H$, can be prepared in accordance with the following reaction scheme as described in Drugs of the Future, Vol. 8, No. 5, pages 395 and 396, (1983).

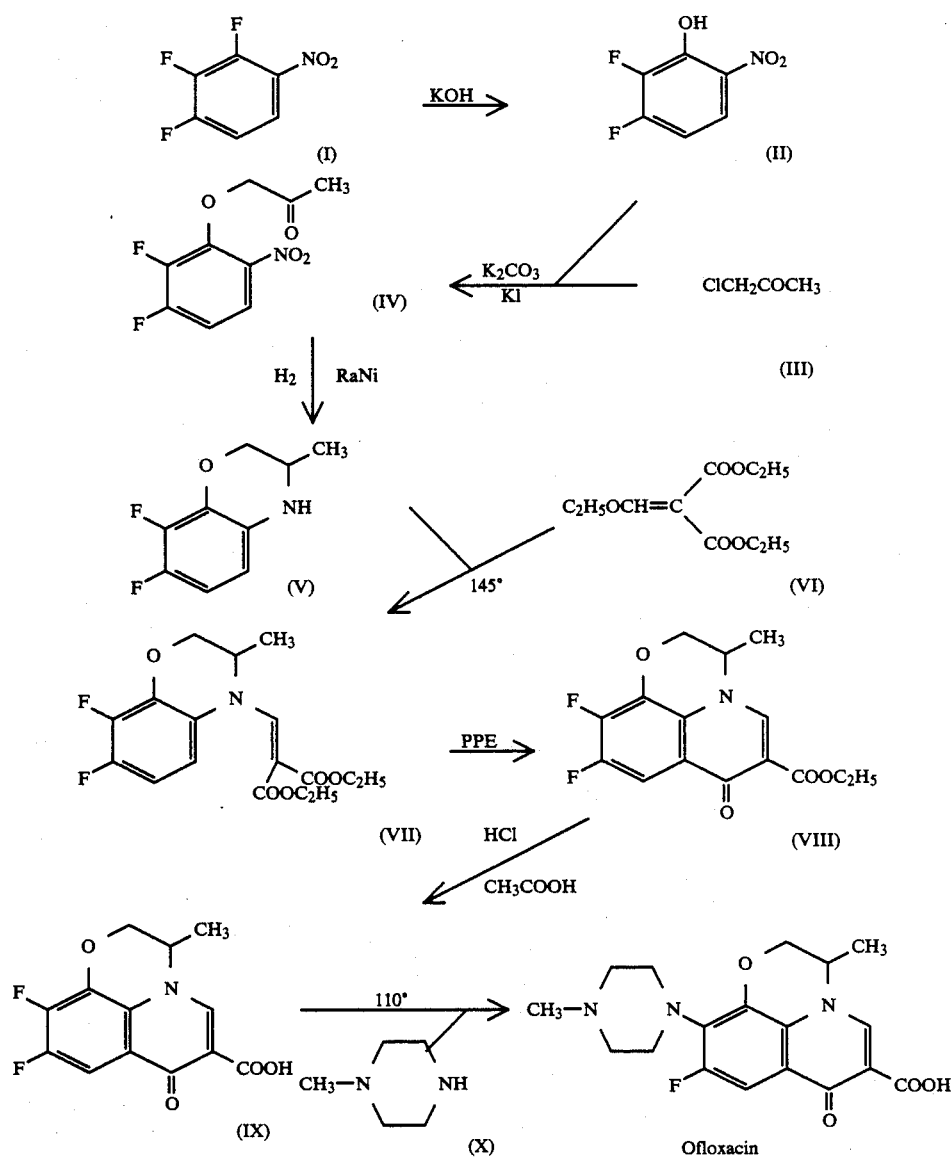

Using the above preparative procedure, the reductive cyclization of (IV) with $H_2$ over RaNi in ethanol produces only the racemate (R,S) 7,8-difluoro-2,3-dihydro-3-methyl-4H-benzoxazine (V) and hence this leads to the production of the racemate (R,S) compounds only.

In pharmacology, one enantiomer of a biologically active racemic mixture may possess biological activity, while another enantiomer of the same compound has little or no such activity. Sometimes one enantiomer possesses a certain undesirable side effect while the other enantiomer does not. Hence, an efficient route that can produce optically pure enantiomers is desirable.

DESCRIPTION OF THE PREFERRED EMBODIMENTS

It has now been discovered that the individual enantiomer (S) or (R) as well as the racemate (R,S) of benzoxazine 6-carboxylic acids of formula (A) which has a chiral center at the 3 position can be prepared very efficiently in accordance with the reaction scheme (I), in which $R_1$ is hydrogen, $C_1$ to $C_6$ alkyl or benzyl group, $R_2$ is $C_1$ to $C_6$ alkyl; $R_3$ is $C_1$ to $C_6$ alkyl or benzyl; Z is selected from the group of the formula:

where $R_4$ and $R_5$ are each independently selected from hydrogen, alkanoyl, alkanoylamido and amino-substituted $C_1$ to $C_6$ alkyl; $C_1$ to $C_{10}$ alkyl and substituted derivatives thereof; or $R_4$ and $R_5$ form together with the nitrogen a substituted or unsubstituted aliphatic heterocyclic ring containing 5 to 7 atoms with 1 or 2 hetero atoms selected from S, O, N and combinations thereof. The substituted heterocyclic ring is substituted by one or more of hydrogen, halogen, $C_1$ to $C_6$ alkyl, $NH_2$, amino $C_1$–$C_6$ alkyl, hydroxy $C_1$–$C_6$ alkyl and an amino group of formula

where $R_6$ and $R_7$ are each independently se $C_1$–$C_4$ alkyl, (5-methyl-2-oxo-1,3-dioxolen-4-yl) methyl, hydrogen, alkanoyl. Each X is independently identical or non-identical halogens, preferably each X is a fluorine atom.

Illustrative of such aliphatic heterocyclic groups are piperazinyl groups, piperidinyl groups, pyrolidinyl groups, morpholino groups, thiomorpholino groups, and homopiperazinyl groups (i.e., hexahydro-1-H--1,4-diazepinyl). As used herein, the term "halogen" refers to chloro, bromo, fluoro, and iodo groups, while the term "$C_1$ to $C_6$ alkyl" refers to lower alkyl groups, including methyl, ethyl, propyl, isopropyl, butyl, etc.

As used herein, $C_1$ to $C_{10}$ alkyl includes both branch or straight chained alkyl. Representative of halo-substituted and hydroxy substituted $C_1$ to $C_{10}$ alkyls include chloromethyl, chloroethyl, chlorpropyl, hydroxyethyl, trifluoromethyl, etc.

As used herein, the term "alkanoyl" refers to $R_{12}$—CO— wherein $R_{12}$ is $C_1$ to $C_6$ alkyl.

As used herein, the term "alkanoylamido" refers to $R_{13}$-CONH—wherein $R_{13}$ is $C_1$ to $C_6$ alkyl.

The present invention additionally relates, in part, to novel compounds of the formulae:

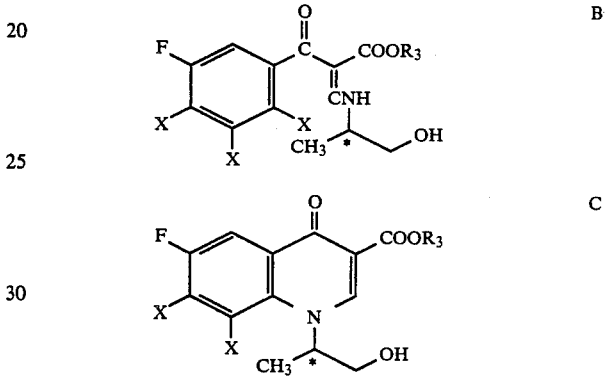

wherein $R_3$ is as defined above, each X is independently selected from a halogen. Preferably each X is fluorine atom.

As for formula B and C, the configuration at the position with an asterisk indicates (R,S) racemate, and (R) or (S) enantiomers. These compounds are useful intermediates in the production of compound of formula (A). Preferred compounds of formula (B) and (C) are those compounds in which $R_3$ is ethyl and X is a fluorine atom.

In addition to the foregoing compounds, the enatiomers (R) and (S) of (A) include the pharmaceutically acceptable salts of (A).

Scheme I

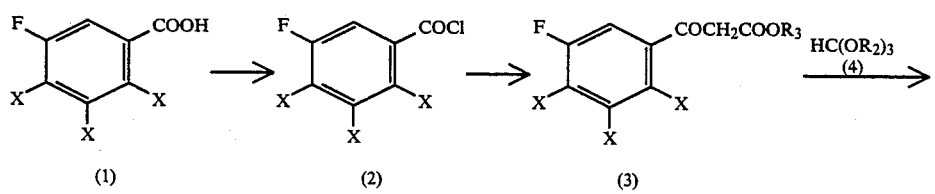

Scheme I -continued

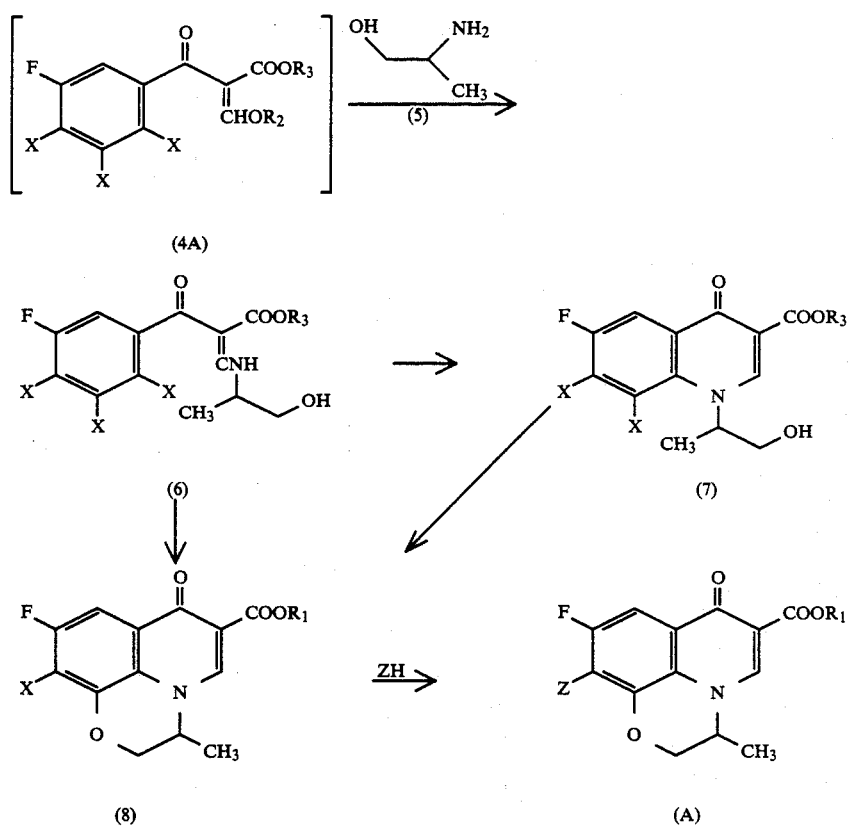

In accordance with reaction scheme I, the 2,3,4-trihalo-5-fluorobenzoic acid (1) is treated with thionyl chloride to produce the corresponding acid chloride (2). Displacement of the acid chloride (2) with malonic acid half ester in the presence of n-butyl lithium yields the 8-ketoester (3).

The β-ketoester (3) is then treated with a trialkylorthoformate (4) in the presence of an acid anhydride, preferably acetic anhydride, yielding 4A (alkyl-2-(2′,3′,4′,5′-tetrahalo benzoyl)-3-alkoxyacrylate). Reaction of 4A with D,L or (S)—(+) or R—(—)-2-amino-1-propanol (5) to obtain the enaminoketoester (6). Reaction with the trialkylorthoformate (4) is preferably conducted at elevated temperatures, such as from about 50° C. to about 150° C., preferably from about 100° C. to about 140° C., to obtain an oily liquid (shown in brackets in the reaction scheme), which may be isolated or unisolated, as desired. $R_2$ in the trialkyl orthoformate is an alkyl, preferably $C_1C_4$ alkyl. Reaction of the oily liquid 4A with the D,L or (S)—(+) or R—(—)-2-amino-1-propanol (5) is preferably conducted in an appropriate aprotic or nonaprotic solvent, preferably methylene chloride or tetrahydrofuran, and may be conducted at room or suitable elevated temperature, as desired.

The enaminoketoester (6) is then cyclized, such as by treatment with two mole equivalents of an alkali metal hydride alkoxide a an elevated temperature (e.g. 40° to 145° preferably about 70° C. to obtain the (RS),(S) or (R)-9-fluoro-3-methyl-10-halo-7-oxo-2,3-dihydro-7H-pyrido[1,2,3-de]-1,4-benzoxazine-6-carboxyl ic acid ester (8) ($R_1$=alkyl). Alkali metal hydrides or alkoxides for use in this particular process include sodium hydrode, potassium hydride, or potassium is conducted in the presence of an aprotic solvent, such as dimethoxyethane, bis(2-methoxyethyl) ether, dimethylformamide, tetrahydrofuran or chlorobenzene, and is preferably conducted at temperatures of about 40° C. to about 145° C., more preferably at the reflux temperature of the solvent employed, 70° C. reflux temperature being preferred.

Displacement of the halogen at the number 10 position of the ester (8) with a substituted amine, ZH, followed by hydrolysis yields the condensation product (R,S) racemate or (R) or (S) enantiomers of 9-fluoro-3-methyl-10-substituted amino-7-oxo-2,3-dihydro-7H-pyri [1,2,3-de]-1,4-benzoxazine-6-carboxylic acid (A).

The condensation reaction may be performed by heating a compound of the formula (8) with a substituted amine, ZH, at a temperature of from 20° C. to 200° C., and preferably from 40° C. to 90° C., in the presence of a suitable organic solvent such as pyridine, chloroform, dimethylsulfoxide, sulfolane, dimethylformamide, dimethylacetamide, 1-methyl-2-pyrrolidinone. It is desirable to carry out the reaction in the presence of an acid-acceptor such as triethylamine, potassium carbonate and the like at a molar ratio of 1.0 to 1.2 mole of the acid-acceptor per mole of the compound of the formula (8). The reagent compounds of the formula "ZH" as defined above can also be used as an acid acceptor in which 2 or more molar excess of such a reagent is used.

Since $R_1$ will be alkyl or benzyl in compound 8 under this first reaction scheme, compound A wherein $R_1$ is hydrogen can be produced from the corresponding ester by hydrolysing the ester either with a base like sodium hydroxide or potassium hydroxide, or an acid such as hydrochloric acid.

Alternately, compound (8) wherein $R_1$=hydrogen can be obtained from compound (6) by controlled cyclization with two mole equivalents of a metal hydride or alkoxide as defined above at a low temperature (e.g. 10°-35° C., preferably 20° C.) is dimethylsulfoxide or other suitable organic solvent such as tetrahydrofuran, dimethylformamide to yield compound (7).

Treatment of comound (7) with an alkali metal or alkaline earth metal hydroxide in tetrahydrofuran or other suitable organic solvent such as dimethoxyethane at elevated temperature (eg 50°-120° C., preferably 65° C.-75° C.) yields compound (8) ($R_1$=H). In other words, such a treatment of compound 7 cyclizes the compound to form the third ring and simultaneously hydrolyze the $R_3$ ester to the acid (R=H). Displacement of 10-halogen of the acid (8) ($R_1$=H) with a compound of the formula ZH yields the (R,S) (racemate) or (R) or (S) enantiomers of 9-fluoro-3-methyl-10-substituted amino-7-oxo-2,3-dihydro-7H-pyrido [1,2,3-de]-1,4-benzoxazine-6-carboxylic acid A. ($R_1$=H).

The foregoing may be better understood from the following examples, which are presented for purposes of illustration and are not intended to limit the scope of the inventive concepts. Z in the following examples is N-methyl piperazinyl, but other compounds within the scope of the present invention can be prepared making the appropriate substitutions for N-methyl piperazinyl. As used in the following examples, the references to compounds, such as (1), (2), (3), etc., and to substituents, such as R, $R_1$, $R_2$, etc., refer to the corresponding compounds and substituents in the foregoing reaction scheme I.

EXAMPLE 1

(−)-9-fluoro-3-S-methyl-1-(4-methyl-1-piperazinyl)-7-oxo-2,3-dihydro-7H-pyrido[1,2,3-de]-1,4-benzoxazine-6-carboxylic acid (A).

(a) To a solution of 14.5 g of 2,3,4,5-tetraflurobenzoic acid in 152 ml. of thionyl chloride is added 3 drops of dimethylformamide. After refluxing for 4 hours, the reaction mixture is evaporated to dryness to give 15.5 g of the acid cloride.

A solution of 2.6M n-butyl lithium in hexanes is added dropwise to a mixture of 20.0 g of malonic acid monoethyl ester (a mino-alkylmalonate) and 10 mg of 2,2' biquinoline in 400 ml tetrahydrofuran under $N_2$ atmosphere at −50° C. The temperature is allowed to warm to −5° C. When the brown color persists (a total of 120 ml of n-butyl lithium solution used) the temperature was again lowered to −55° C. The acid chloride from above is mixed with 75 ml tetrahydrofuran and the acid chloride solution is added dropwise to the mixture. The reaction is stirred for an additional 1 hour. The reaction mixture is allowed to warm to room temperature, and then is poured into 400 ml ether and is extracted with 200 ml 1 N HCl solution. The ether-THF layer is separated and washed with dilute cold sodium bicarbonate. The organic layer is dried over magnesium sulfate and then evaporated to obtain an orange oil (18.4 g) of the β-ketoester (3) ($R_3$=$C_2H_5$, X=F).

(b) A solution of ethyl-2,3,4,5-tetrafluorobenzolyacetate (3) ($R_3$=$C_2H_5$,X=F) (400 mg, 1.51 mmol) in acetic anhydride (0.9 ml) and triethyl orthoformate (0.5 ml. 444 mg. 3 mmol) (4) ($R_2$=$C_2H_5$) was heated at 100° C. for 2 hr. The reaction mixture was concentrated under high vacuum to leave an oily residue, which was diluted with toluene (2ml) and concentrated. This process was repeated 2 more times to afford 2-(2,3,4,5-tetrafluorobenzoyl)-3-ethoxyacrylate (4A) as an oil. To a stirred solution of (4A) (without further purification) in dry methylene chloride (5 ml) was added (+)-S-2-aminopropanol (S-alaninol) (5) (2S).(0.19 ml, 180 mg., 2.4% mmol) in $CH_2Cl_2$ and the reaction mixture was stirred at room temperature for 30 minutes or until TLC showed the absence of (3) in the reaction mixture. The reaction mixture was concentrated under reduced pressure to leave an oily residue, which was purified by preparative layer chromatography (silica gel) to afford an analytically pure oil (6) ($R_3$=$C_2H_5$, X=F): 300 mg, 57%, (α)D 25+25.3 (c 0.15); IR (nujol): 3450 (OH and NH), 1670 (C=0) and 1620 (Ar.) $Cm^{-1}$. H NMR ($CDCl_3$):δ0.85 (t, 3H, $CH_2CH_3$), 2.30 (bs, 1H, OH), 3.35 (m, 4H, $CH_2OH$ & $CH_2CH_3$), 3.70 (m, 1H, $CHCH_3$), 8.05 (dd, 1H, J=14 & 3 Hz, $C_5$-H) and 8.15 (s, 1H, C -H); EIMS: m/z 349 ($M^+$), 318 ($M^+$-CH OH), 272 ($M^+$-$CH_2OH$,-$OC_2H_5$), 177 $C_6HF_4$-C=0, base peak); HRMS: m/z M 349.09409 (calcd. for $C_{15}H_{15}F_4NO_4$ m/z 349.09361).

(c) To a stirred soln.of (+)-ethyl-2-(2,3,4,5-tetrafluorobenzoyl) tetrafluorobenzoyl)-3-(1'-S-hydroxymethylethylamino) -acrylate (6) ($R_3$=$C_2H_5$, X=F) (190 mg, 0.544 mmol) in dry DMSO (3ml) was added in portions NaH (50% mineral oil suspension, 24.5 mg, 1.02 mmol) and the reaction mixture was stirred at room temperature for 3 hours. The reaction mixture was diluted with an excess of $H_2O$ (20 ml) and was extracted from $CH_2Cl_2$ (4 x 10 ml). The combined $CH_2Cl_2$ layer was washed with $H_2O$ (2×5 ml), dried ($Na_2SO_4$) and concentrated to leave a residue, which was again washed with $H_2O$ (0.5 ml) and the resulting solid was crystallized from a mixture of $CH_2Cl_2$-ether to afford the S enantiomer (7) ($R_3$=$C_2H_5$, X=F) (105 mg, 59%), mp 170-75° C.:αD25−28°(C 0.2); IR (Nujol): 3450 (OH), 1700(C=0) and 1620(Ar.) $Cm^{-1}$. H NMR ($CDCl_3$):δ1.35 (t, 3H, $CH_2CH_3$), 1.55 (s, 1H, OH, exchangeable with $D_2$). 4.15 - 4.65 (m, 4H $CH_2OH$ & $CH_2CH_3$), 5.25 (m, 1H, $C_5$-H), 7.40 (dd, 1H, J=14 & 3 Hz, C-H) and 8.65 (s, 1H, $C_2$-H): EIMS: m/z 329 ($M^+$), 29 ($M^+$-$CH_2OH$).

(d) To a stirred solution of the above S enantiomer (7) ($R_3$=$C_2H_5$, X=F) (75 mg, 0.227 mmol) in THF (12 ml) was added a 10% aqueous soln. of KOH (2 ml) and the reaction mixture was heated at 65°-70° C. for 2 hours (until TLC showed the absence of (7) in the reaction mixture). The reaction mixture was concentrated under reduced pressure to remove THF and the resulting aqueous basic layer was acidified to pH 4-5 by the addition of dilute HOAc to afford a white precipitate, which was filtered and washed with $H_2O$ and then with ether to afford a pure solid S enantiomer (8) ($R_1$=H, X=F) (45 mg, 70%), mp>280°C(d):αD25, −66.5°(c 0.1); IR (nujol): 1700 (C=0) and 1610 (Ar.) $Cm^{-1}$; EIMA: m/z 281 ($M^+$) , 253 ($M^+$-CO), 237 (M −COO): CIMS-$CH_4$: m/z 282($M^+$+1):.

(e) To a solution of (−)-9,10-difluoro-3-S-methyl-7-oxo-2,3-dihydro-7H-pyrido-(1,2,3-de)-1,4-benzoxaz ine-6-carboxylic acid (8) ($R_1$=H, X=F) (1g) in 5 ml pyridine was added in 0.85 g of N-methylpiperazine and the reaction mixture was heated at 70° C. for 8 hours. The reaction mixture was concentrated under high vacuo to leave a residue, which was taken in toluene 30 ml and concentrated. This process was repeated 2 more times to afford a solid (−)-9-fluoro-3-S-methyl-10-(4-methyl-1-piperazinyl)-7-oxo-2,3-dihydro-7H-pyrido-(1,2,3-de)-1,41-benzoxazine-6-carboxylic acid (A). ($R_1=H$, Z=N-methylpiperazinyl).

(f) Alternately, the S-enantiomer (−)-9,10- difluoro-3-S-methyl-7-oxo-2,3-dihydro-7H-pyrido-(1,2,3-de)-1,4-benzoxazine-6-carboxylic acid (8) ($R_1=H$, X=F) can be prepared from (+)-ethyl-2-(2,3,4,5-tetra-fluorobenzyl)-3-(11 S-hydroxy-methylethylamino)acrylate (6) ($R_3=C_2H_5$, X-F) as described below:

To a cold solution of 15 g of (+)-ethyl-2-2,3,4,5-tetra-fluorobenzayl)-3-(11-S-hydroxymethylethyl amino)-acrylate (6)($R_3C_2H_5$, X=F) in 200 ml tetrahydrofuran was slowly added 3.45 g of a 60% sodium-in-oil suspension. The mixture is refluxed for 24 hours and was cooled and diluted with water to a volume of 1.5 liters. The mixture was then filtered and the solid was washed with a 1:1 hexane/ether solution to obtain (−)-ethyl-9,10-difluoro-3-S-methyl-7-oxo-2,3-dihydro dihydro-7H-pyrido-(1,2,3-de)-1,4-benzoxazine-6-carboxylate (8) ($R_1=C_2H_5$, X=F).

The above solid (8) ($R_1=C_2H_5 X=F$) was hydrolysed by dissolving in 200 ml tetrahydrofuran and a solution of 1.72 g sodium hydroxide in 20 ml water was added and the mixture was heated at 80° C. for 3 hours. The solvent was removed and the residue was dissolved in 750 ml water and the solution was acidified with 1 N HCl to pH 1. The precipitate was filtered yielding the S enantiomer (8) ($R_1=H$, X=F).

(g) To a solution of 3 g of (−) ethyl 9,10-difluoro-3-S-methyl-7-oxo-2,3-dihydro-7H-pyrido[1,2,3 -de]-1,4-benzoxazine-6-carboxylate (8) ($R_1=C_2H_5$, X=F) in 15 ml pyridine is added in 2.5 g of N-methylpiperazine. The mixture is heated at 55° C. for 8 hours. The solvent is then removed by evaporation at reduced pressure and the solid is washed with ether and dried. Ether is then added, and the mixture is warmed for about 10 minutes and is cooled. ¼ volume of hexane is added and the solid is filtered. The solid is then dissolved 30 ml of THF and a sodium hydroxide solution (0.6 g) in 20 ml water. The mixture is heated at 80° C. for 1½ hours.

The clear solution is evaporated to dryness under reduced pressure. The solid is dissolved in 50 ml water and 1.5 ml acetic acid is added. The resulting dried yielding (−)-9-fluoro-3-S-methyl-10-(4-methyl-1-piperazinyl) 6-carboxylic acid (A). (Z =N-methylpiperazinyl; $R_1=H$)

EXAMPLE 2

(+)-9-fluoro-3-R-methyl-10-(4-methyl-1-piperazinyl)-7-oxo-2,3-dihydro-7H-pyrido [1,2,3-de]-1,4-benzoxazine-6-carboxylic acid.

(a) The procedure of Example 1 (a and b) is repeated, replacing (+)-S-2-amino-1-propanol in 1 (b) with (−)-R-2-amino-1-propanol to obtain (−)-Ethyl-2-(2,3,4,5-tetrafluorobenzoyl)-3-(1′-R-hydroxyme thylethylamino)acrylate (6) ($R_3=C_2H_5$, X=F).

(b) In the described fashion as Examples 1(c) and (d), the preceding (R) enantiomer of compound (6) yields (+) 9,10-difluoro-3-R-methyl-7-oxo-2,3-dihydro-7H-pyrido [1,2,3-de]-1,4-benzoxazine-6-carboxylic acid (8) ($R_1=H$, X=F).

(c) the procedure of Example 1 (e) is repeated using the preceding compound (8) ($R_1=H$, X=F), to obtain the (+)-9-fluoro-3-R-methyl-10-(4-methyl-1-piperazinyl)-7-oxo-2,3-dihydro-7H-pyrido [1,2,3-de]-1,4-benzoxazine-6-carboxylate acid (A). (Z=N-methylpiperazinyl; $R_1=H$)

EXAMPLE 3

(+)-Ethyl(6,7,8-trifluoro-1-(1-R-hydroxy-2-propyl)-1,4-4-oxo-qinoline-3-carboxylate.

As in the procedure described in Example 1 (a,b, and c) replacing (+)-S-2-amino-1-propanol in 1(b) with (−)-R-2-amino-1-propanol, one can obtain the (+) Ethyl 6,7,8-trifluoro-1-(1-R-2-hydroxy-2-propyl)-1,4-dihydro-4-oxo-quinoline-3-carboxylate (7) ($R_3=C_2H_5$, X=F).

EXAMPLE 4

(+/−)-9-fluoro-3-methyl-10-(4-methyl-1-piperazinyl)-7-oxo-2,3-dihydro-7H-pyrido [1,2,3-de]-1,4-benzoxazine-6-carboxylic acid.

(a) The procedure of Example 1 (a) and (b) is repeated, replacing (+)-S-2-amino-1-propanol in 1 (b) with (+)-R,S-2-amino-1-propanol to obtain the racemicenaminoketoester (6) ($R_3=C_2H_5$, X=F).

(b) In the procedure described in Example 1(c) and (d), the preceding (R,S) racemate of compound (6) yields (+) 9,10-difluoro-3-R,S--methyl-7-oxo-2,3-dihydro-7H-pyrido [1,2,3-de]-1,4-benzoxazine-6-carboxylic acid (8) ($R_1=H$, X=F).

(c) The procedure of Example 1 (e) is repeated using the preceding compound (8) (Rl=H, X=F), to obtain the (+)-9-fluoro-3-S-methyl-10-(4-methyl-1-piperazinyl)-7-oxo-2,3-dihydro-7H-pyrido [1,2,3-de]-1,4-benzoxazine-6-carboxylic acid.

EXAMPLE 5

(+)-Ethyl 6,7,8-trifluoro-1-(1-R,S-hydroxy-2-propyl)-1,4-dihydro-4-oxo-quinoline-3-carboxylate.

In the described fashion as Example 1 (a, b and c) replacing (+)-S-2-amino-1-propanol in 1 (b) with (±) R,S-amino-1-propanol, one can obtain the (±) Ethyl 6,7,8-trifluoro-1-(R,S-hydroxy-2-propyl)-1,4-dihydro-4-oxo-quinoline-3-carboxylate (7) (R -$C_2H_5$, X=F).

It can be seen from the foregoing that a novel process for making racemic and optically active ofloxacin and related derivatives and novel intermediates used in the process are disclosed. The examples are not intended to limit the scope of the claims which are defined in the following claims.

What is claimed is:

1. A compound of the formula

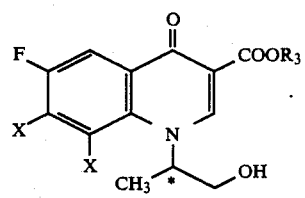

wherein the carbon atom marked by the asterisk has the (R,S), R, or S configuration; $R_3$ is $C_1$–$C_6$ alky; and each X is independently selected from a halogen.

2. A compound of claim 1 wherein $R_3$ is ethyl, and X is fluoro.

3. The compound of claim 1 wherein the asterisked carbon has the R configuration.

4. The compound of claim 1 wherein the asterisked carbon has the S configuration.

* * * * *

UNITED STATES PATENT AND TRADEMARK OFFICE
CERTIFICATE OF CORRECTION

PATENT NO. : 4,826,985

DATED : May 2, 1989

INVENTOR(S) : Lester A. Mitscher and Daniel T. Chu

It is certified that error appears in the above-identified patent and that said Letters Patent is hereby corrected as shown below:

Column 2, line 65: Replace "H$_2$over" with --H$_2$ over--

Column 10, line 60: Replace "C$_1$-C alky;" with --C$_1$-C$_6$ alkyl;--

Signed and Sealed this

First Day of January, 1991

Attest:

HARRY F. MANBECK, JR.

Attesting Officer     Commissioner of Patents and Trademarks